United States Patent
Morikawa et al.

(10) Patent No.: US 9,638,674 B2
(45) Date of Patent: May 2, 2017

(54) AUTOSAMPLER

(71) Applicant: SHIMADZU CORPORATION, Kyoto-shi, Kyoto (JP)

(72) Inventors: Tsuyoshi Morikawa, Kyoto (JP); Tsutomu Okoba, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 0 days.

(21) Appl. No.: 14/768,463

(22) PCT Filed: Jan. 15, 2014

(86) PCT No.: PCT/JP2014/050588
§ 371 (c)(1),
(2) Date: Aug. 18, 2015

(87) PCT Pub. No.: WO2014/132687
PCT Pub. Date: Sep. 4, 2014

(65) Prior Publication Data
US 2015/0377843 A1    Dec. 31, 2015

(30) Foreign Application Priority Data

Feb. 27, 2013 (JP) .................................. 2013-036890

(51) Int. Cl.
*G01N 30/24* (2006.01)
*G01N 30/38* (2006.01)
(Continued)

(52) U.S. Cl.
CPC ............. *G01N 30/24* (2013.01); *G01N 30/20* (2013.01); *G01N 30/38* (2013.01); *G01N 2030/027* (2013.01)

(58) Field of Classification Search
CPC ..................................................... G01N 30/24
See application file for complete search history.

(56) References Cited

U.S. PATENT DOCUMENTS 5,814,742 A * 9/1998 Vissers .................. G01N 30/24
73/64.56
6,344,172 B1 * 2/2002 Afeyan ................ G01N 30/461
210/198.2

(Continued)

FOREIGN PATENT DOCUMENTS

JP    6-235722 A    8/1994
JP    6-273403 A    9/1994
(Continued)

OTHER PUBLICATIONS

International Search Report dated Apr. 1, 2014, issued in counterpart International Application No. PCT/JP2014/050588 (2 pages).

(Continued)

*Primary Examiner* — Lisa Caputo
*Assistant Examiner* — Tran M Tran
(74) *Attorney, Agent, or Firm* — Westerman, Hattori, Daniels & Adrian, LLP (57) ABSTRACT

An autosampler includes a flow path switching valve to which a sample push unit and an analysis flow path are connected, a sample loop connected to the flow path switching valve, a sampling needle connected to the flow path switching valve, a metering pump connected to the flow path switching valve, and a control unit for controlling operations of the flow path switching valve and the metering pump. The control unit includes an injection volume addition unit for adding up injection volume of a same sample component injected into the sample loop.

6 Claims, 9 Drawing Sheets

(51) Int. Cl.
*G01N 30/20* (2006.01)
*G01N 30/02* (2006.01)

(56) References Cited

U.S. PATENT DOCUMENTS

| | | | | |
|---|---|---|---|---|
| 6,485,642 B2* | 11/2002 | Kaito | ............... | G01N 30/34 |
| | | | | 210/101 |
| 6,942,793 B2* | 9/2005 | Ito | ............... | G01N 30/463 |
| | | | | 210/143 |
| 7,797,989 B2* | 9/2010 | Swart | ............... | G01N 30/20 |
| | | | | 73/61.56 |
| 7,862,716 B2* | 1/2011 | Zelechonok | ............... | G01N 30/40 |
| | | | | 210/143 |
| 8,017,015 B2* | 9/2011 | Clarke | ............... | B01J 20/28083 |
| | | | | 210/198.2 |
| 8,074,494 B2* | 12/2011 | Vorm | ............... | B01D 15/1871 |
| | | | | 73/61.53 |
| 8,191,404 B2* | 6/2012 | Ono | ............... | G01N 30/24 |
| | | | | 73/61.55 |
| 8,770,046 B2* | 7/2014 | Maeda | ............... | G01N 30/20 |
| | | | | 73/863.01 |
| 8,794,052 B2* | 8/2014 | Maeda | ............... | G01N 30/20 |
| | | | | 73/61.55 |
| 9,003,868 B2* | 4/2015 | Ono | ............... | G01N 30/24 |
| | | | | 73/61.55 |
| 9,228,982 B2* | 1/2016 | Ebsen | ............... | G01N 30/20 |
| 2008/0314129 A1* | 12/2008 | Schultz | ............... | G01N 30/80 |
| | | | | 73/61.55 |
| 2012/0024048 A1 | 2/2012 | Maeda | | |
| 2012/0132013 A1* | 5/2012 | Glatz | ............... | G01N 30/20 |
| | | | | 73/863.02 |
| 2013/0146479 A1* | 6/2013 | Brouwer | ............... | G01N 24/08 |
| | | | | 205/780.5 |

FOREIGN PATENT DOCUMENTS

| | | |
|---|---|---|
| JP | 3476417 B2 | 12/2003 |
| JP | 3109378 U | 5/2005 |
| WO | 2010/119801 A1 | 10/2010 |

OTHER PUBLICATIONS

Office Action dated May 5, 2016, issued in Chinese Patent Application No. 201480010024.3, with English translation. (11 pages).

* cited by examiner

Pre-Treatment Program 16 v.load　　　　(switchs HPV to sample load position)

vial sn　　　 (moves needle above vial position)

pickup.s av, ss (picks up air gap and starts volume calculation)

n.strks ns　　(move down needle and detects liquid level)

aspir iv, ss　 (aspirates sample)

pickup.e nv, ss (moves sample edge to HPV and ends volume calculation)

event 1　　　(event signal for time program start)

wait 2.0　　　(wait 2 minutes for pumps purge)

s.inj　　　　　(sends start signal and switchs HPV
　　　　　　　　　　　　　to sample injection position)

irinse rv, rs　 (rinse sample loop and needle)

Single-Fraction Batch Table 17

| Vial Position | Injection Volume (μL) | Method |
|---|---|---|
| 1 | 10000 | Method Including Pre-Treatment Program 16 |

Fig. 7A

Pre-Treatment Program 18 v.load          (switchs HPV to sample load position)

vial sn         (moves needle above vial position)

pickup.s av, ss (picks up air gap and starts volume calculation)

n.strk ns       (move down needle)

aspir iv, ss           (aspirates sample)

check.vol off   (disables volume calculation)

start           (sends start signal and purges syringe)

Pre-Treatment Program 19 check.vol on    (enables volume calculation)

vial sn         (moves needle above vial position)

n.strk ns       (move down needle)

aspir iv, ss           (aspirates sample)

check.vol off   (disables volume calculation)

start           (sends start signal and purges syringe)

Fig. 7B

Pre-Treatment Program 20 check.vol on    (enables volume calculation)

vial sn    (moves needle above vial position)

n.strk ns    (move down needle)

aspir iv, ss    (aspirates sample)

pickup.e nv, ss  (moves sample edge to HPV and ends volume calculation)

event 1    (event signal for time program start)

wait 2.0    (wait 2 minutes for pumps purge)

s.inj    (sends start signal and switchs HPV to sample injection position)

irinse rv, rs    (purges air gap)

Multi-Fraction Batch Table

| Vial Position | Injection Volume (μL) | Method |
|---|---|---|
| 1 | 30000 | Method Including Pre-Treatment Program 18 |
| 2 | 30000 | Method Including Pre-Treatment Program 19 |
| 3 | 30000 | Method Including Pre-Treatment Program 19 |
| 4 | 5000 | Method Including Pre-Treatment Program 20 |

AUTOSAMPLER

TECHNICAL FIELD

The present invention relates to, for example, an autosampler, and to an autosampler for injecting a sample into a sample concentration device based on a trap column or an analysis device such as a liquid chromatograph provided with such a sample concentration device, and more particularly, to a technique for controlling an autosampler for injecting a single component which has been separated into several fractions by a preparative LC (liquid chromatograph).

BACKGROUND ART

As a method of extracting synthesized compounds as a single component, generally, a method of using a preparative liquid chromatograph, among liquid chromatographs, and performing separation/fractionation, and then performing concentration is used.

With respect to concentration, although a vacuum evaporator is also used, concentration by a trap column is often used because if an elimination column is used in combination, additives and the like may be eliminated (see Patent Document 1).

Generally, in the case of trapping a sample in a trap column, if the sample concentration is high, or the solvent strength of a sample solvent is high, trapping is difficult, and thus, a diluted sample is delivered to the trap column so as to facilitate trapping.

Dilution may be performed at the time of adjusting the sample, but in the case where the sample volume after dilution is excessively high, processing is difficult, and thus, dilution is performed online. In online dilution, a flow path similar to the flow path structure of a sample concentration device as shown in FIGS. 1 and 4 is used as an embodiment.

Figure 1:
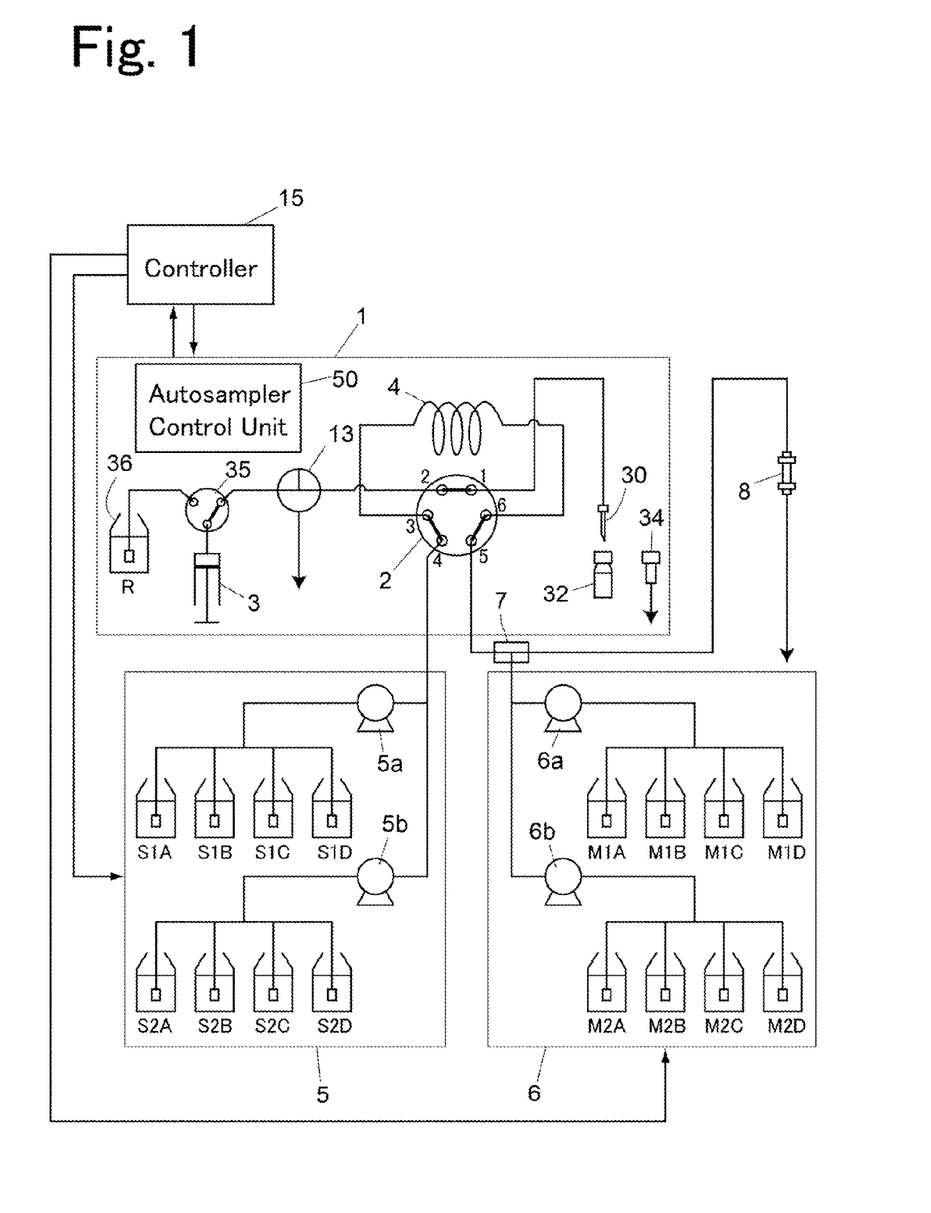
FIG. 1 is a schematic flow path diagram showing a sample concentration device including an autosampler of an embodiment in a flow path state at the time of idling or in a flow path state at the time of injection/sample trapping.
Figure 4:
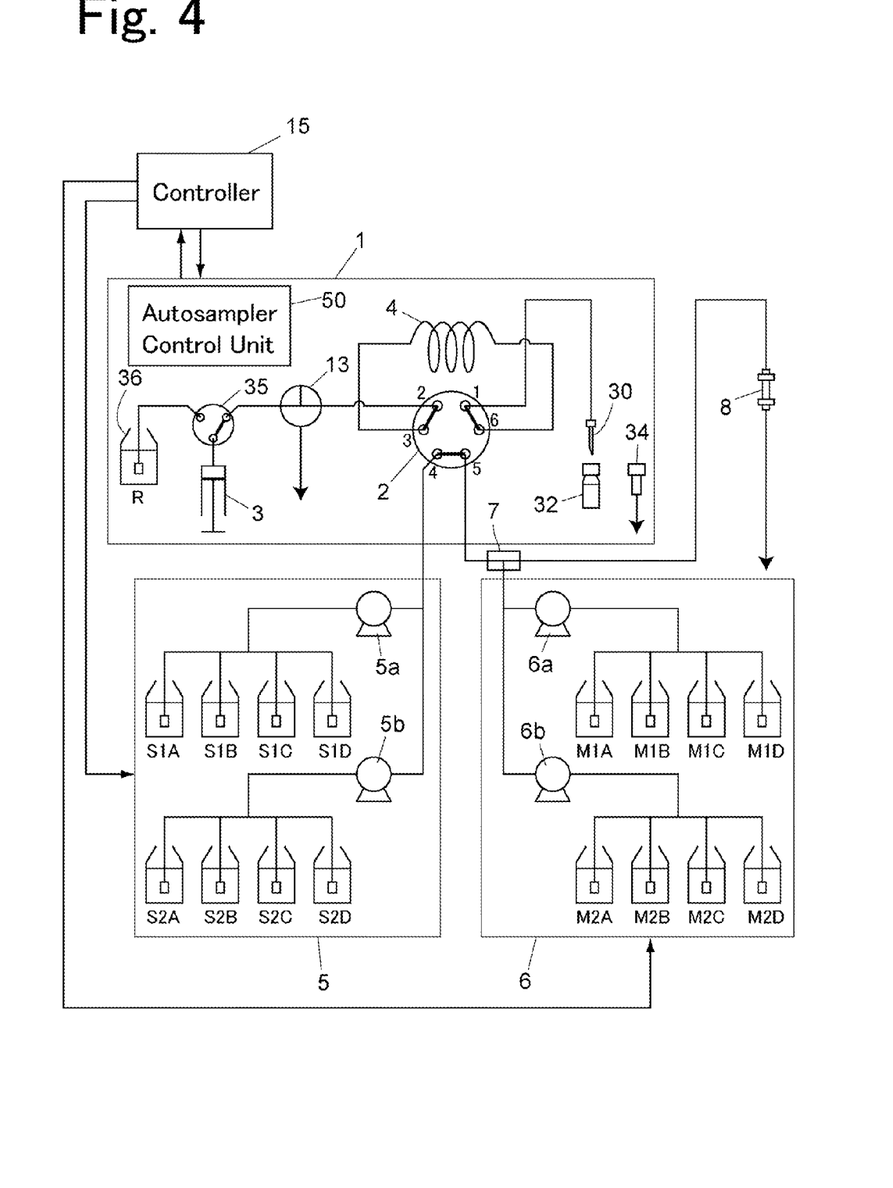
FIG. 4 is a schematic flow path diagram showing the sample concentration device in a flow path state at the time of sample metering.

In FIG. 1, a high-pressure valve 2 is switched to an injection position according to which a sample loop 4 is incorporated in a main flow path including a sample push unit 5 and a trap column 8, and in FIG. 4, the high-pressure valve 2 is switched to a metering position according to which the sample loop 4 is incorporated to a metering flow path including a syringe pump 3 and a sampling needle 30.

According to such a sample concentration device, the high-pressure valve 2 is switched from an idling state (the high-pressure valve 2 is in the state in FIG. 1, which is the same as the injection position) to a sample metering state in FIG. 4, and a sample is drawn by the syringe pump 3 at an autosampler 1 and is introduced into the sample loop 4. Next, the high-pressure valve 2 is switched to the injection state in FIG. 1, and the sample in the sample loop 4 is pushed out from the sample loop 4 by a mobile phase delivered from the sample push unit 5. Then, the sample is diluted by being mixed with a diluent (normally, of the same composition as the mobile phase) delivered from the make-up unit 6 at the three-way joint 7 on the main flow path, and is lead to, and trapped in, the trap column 8.

Figure 3:
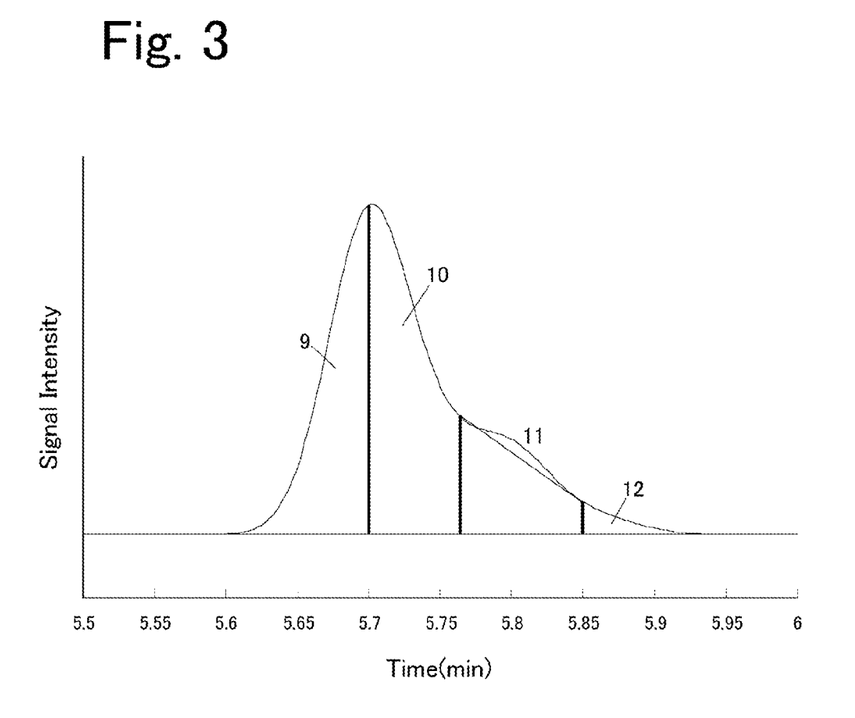
FIG. 3 is a waveform diagram showing example fractionation of two component peaks by a preparative system for obtaining a sample for the sample concentration device.

An example of a sample that is used by such a sample concentration device is a single component sample obtained by separating synthesized compounds by a preparative system. For example, the fractionations for two component peaks according to the preparative system are shown in FIG. 3. In this example, the peak of a component B (retention time: 5.8 min) overlaps a tailing component A (retention time: 5.7 min). When a flow rate of 100 mL/min and a maximum fraction volume of 10 mL for one fraction vial are given as conditions, the upper limit of the volume of the vial is reached in 0.1 minute. Then, in this example, it can be seen that when a fraction 9 reaches the maximum fraction volume 10 mL of a vial #1, it is switched to a fraction 10, and then, before the maximum fraction volume 10 mL of a vial #2 is reached, the rise of a peak of the component B is detected and switching to a fraction 11 is performed, and switching to a fraction 12 takes place when a fall of the peak of the component B is detected.

In the example in FIG. 3, the fractions 9, 10 and 12, which are a single component, are taken as a sample, and are injected to a concentration system based on a trap column, and concentration is performed.

With a general liquid chromatography analysis system, sample injection and the analysis process are programmed according to a table called a batch table (referred to also as a sequence table or a sample set). One row of the batch table corresponds to one analysis, and each row contains the position of a sample vial, the sample volume, and other analysis conditions.

Other analysis conditions include an analysis initial parameter set, a pre-injection processing program for customizing the operation of the autosampler 1 (normally referred to as a pre-treatment program. In the case of not performing customization, a standard pre-treatment operation is internally programmed), a time program (also referred to as an event or an event program), and the like, and normally, these are stored in a parameter set called instrument method. The pre-treatment program may be specified in the batch table independently of the instrument method.

The process in one row of the batch table is performed in the order of downloading of the position of a sample vial, the sample volume and other analysis conditions to the device (download), execution of the pre-treatment program (pre-treatment execution), and execution of a time program and start of recording of a chromatogram (analysis execution).

As programming methods of the example in FIG. 3, there are the following (a) to (d).

(a) The fractions 9, 10 and 12 are transferred to one vial and are taken as one sample, and programming is performed with "one row/one injection".

The "injection" here refers to connection of the sample loop 4 to the main flow path by switching of the high-pressure valve 2 to the injection position after one sample is introduced into the sample loop 4 by the pre-treatment program. In many cases, an event signal (an electrical signal, a communication command, a software instruction) for performing recording start of a chromatogram or a time program is output simultaneously with the switching of the high-pressure valve 2, but the event signal may be output before or after the switching of the high-pressure valve 2.

In this case, according to the instrument method, an "injection" process for one sample is performed by the pre-treatment program, and the sample push unit 5 and the make-up unit 6 are controlled by the time program, and fixation of the sample to the trap column 8 is performed. Here, after the sample is introduced into the sample loop 4, and before the high-pressure valve 2 is switched, an event signal is output to start delivery of a mobile phase and a diluent by the sample push unit 5 and the make-up unit 6 by the time program, and switching of the high-pressure valve 2 is performed after the delivery becomes stable.

(b) Programming is performed assuming "three rows/two loadings, one injection" for the fractions 9, 10 and 12.

The "loading" here means that the high-pressure valve 2 is not switched after a sample is introduced into the sample loop 4 by the pre-treatment program. In the case of this example, one row is one loading, and thus, after the "loading", an event signal is output by the pre-treatment program and the time program is started, but since the sample push unit 5 and the make-up unit 6 do not have to operate, the time program is ended swiftly. Additionally, since the time program is ended swiftly, the autosampler 1, which cannot output an event signal unless the high-pressure valve 2 is switched, may perform a process corresponding to the "loading" in the "injection" process, but detailed description here is omitted.

In reality, an instrument method for sample push for up to the N-1th row and an instrument method for injection for the Nth row are prepared and combined. In the case of this example, "loading" of one sample is performed by the pre-treatment program by the instrument method for sample push for the fractions 9 and 10, and "injection" of one sample and fixation of the sample to the trap column 8 are performed by the pre-treatment program by the instrument method for injection for the fraction 12. The contents of the processing by the instrument method for injection are the same as the contents of the processing by the instrument method of (a). Here, the samples of the fractions 9 and 10 are sent to the trap column 8 together with the sample of the fraction 12.

(c) Programming is performed assuming "one row/two loadings" for the fraction 9 with fixed volume and the fraction 10 with variable volume, and assuming "one row/one injection" for the fraction 12 with variable volume.

In reality, an instrument method for sample push of "one row/N loading (N: 1 or more, N-1 fraction: fixed volume, one fraction: variable volume)" and an instrument method for injection of "one row/one injection" are prepared and combined. In the case of this example, "loading" of one sample with fixed volume and one sample with variable volume (the volume is specified in the batch table) is performed by the pre-treatment program by the instrument method for sample push for the fractions 9 and 10, and "injection" of one sample with variable volume (the volume is specified in the batch table) and fixation of the sample to the trap column 8 are performed by the pre-treatment program by the instrument method for injection for the fraction 12. The contents of the processing by the instrument method for injection are the same as the contents of the processing by the instrument method of (a).

(d) Programming is performed assuming "one row/two loadings, one injection" for the fractions 9, 10 and 12, and "loading" and "injection" are performed by the pre-treatment program of the autosampler included in the instrument method by separately customizing the volumes of the fraction 9, 10 and 12.

According to this method, the instrument method performs, by the pre-treatment program, "loading" of each of the samples of the fractions 9 and 10, and "injection" of the sample of the fraction 12, and performs fixation to the trap column 8. The contents of the processing after introduction into the sample loop 4 are the same as the contents of the processing by the instrument method of (a).

In any of (a) to (d), the make-up unit 6 has to deliver a diluent by the volume several times the actual sample injection volume.

Here, the "actual sample injection volume" that is introduced into the sample loop 4 and injected into the main flow path is the total sample volume in the case where no special pre-treatment is required, and is the volume obtained by adding the volume of an additive to the total sample volume in the case where pre-treatment such as mixing of an additive is to be performed, and specification thereof in advance is difficult. Due to this, normally, instead of the "actual sample injection volume", the "maximum sample injection volume" is defined based on the volume of the sample loop 4 and the number of times of injection into the main flow path, and the maximum fraction volume and the maximum number of fraction vials.

The main objects of a liquid chromatography analysis are separation and analysis, and the retention time of a sample is not dependent on the sample volume, and only the tailing factor determining the elution range of the sample is dependent on the sample volume. Accordingly, in the case of using a specific sample, the analysis time at the liquid chromatography analysis may be assumed to be constant without relying on the sample volume.

With the device control of a liquid chromatography analysis device, an operation may be programmed in the instrument method based on the analysis time and the time program (referred to also as an event or an event program), but control of operating a solvent delivery pump based on the actual sample injection volume cannot be performed.

Accordingly, with the liquid chromatography analysis device, in the case of performing trap concentration, a method of controlling the pump by switching the instrument method prepared for each sample volume range, or a method of controlling the pump by a time calculated with respect to the maximum sample injection volume is used.

PRIOR ART DOCUMENTS

Patent Documents

Patent Document 1: Japanese Patent No. 3476417

SUMMARY OF THE INVENTION

Problems to be Solved by the Invention

In theory, in any of the programming methods (a) to (d), the volume of every fraction may fall below the maximum fraction volume due to superimposition of an interfering component. In a conventional technique, in the case where the actual sample injection volume is one-tenth of the maximum sample injection volume, there is wasteful consumption of solvents of (maximum sample injection volume)×9÷10 for a mobile phase, and (maximum sample injection volume)×(dilution rate−1)×9÷10 for a diluent, and more time is also wastefully consumed as the amount of solvent consumption is increased.

If the maximum sample injection volume is 50 mL, the dilution rate is 5 times, and there is no mixing of additives, delivery of 250 mL of solvent (mobile phase+diluent) becomes necessary per sample, and of this, 225 mL of solvent will be wastefully consumed.

To deliver 250 mL of solvent per sample means that 25 L of solvent becomes necessary for 100 samples, and when considering the burden of preparation and replenishment of solvent and the environmental burden of solvent, in addition to the purchase cost of solvent itself, there is a demand from users to suppress the amount of solvent consumption as much as possible.

To minimize the amount of solvent consumption, a method of dividing the sample volume range, specifying the maximum sample volume and defining the instrument method for each range, and using the instrument method accordingly is used in many cases, but this method requires development and maintenance of many instrument methods.

Furthermore, the fraction volume and the number of fractions of a sample to be concentrated by the trap column depend greatly on the density of the sample, the retention time, and the degree of separation from other components, and cannot be decided unconditionally due to the following reasons.

The following can be said with respect to the peak width of a chromatogram.

(A) The peak width of a single component tends to be wider as the density is higher in the case of the same mobile phase composition and delivery flow rate.

(B) With respect to peak widths of a plurality of components, the peak width tends to be wider for the component with a long retention time in the case of the same mobile phase composition and delivery flow rate and the same density.

(C) The retention time tends to be shorter as the delivery flow rate is greater in the case of the same mobile phase composition.

(D) The retention time may be changed by changing the mobile phase composition in the case of the same delivery flow rate.

Accordingly, the number of fractions of a single component peak is different depending on the conditions of delivery. The number of fractions of a single component peak is also different depending on the sample. The fraction volume and the number of fractions of multiple component peaks except the interfering component peak are also different depending on the sample. This is because the peak widths and the degree of overlapping of peaks are different depending on the sample.

In any of the programming methods (a) to (d), the sample volume is not known in advance, and since there is a possibility of evaporation or that the volume that can be drawn by the autosampler is not reached (a solvent inevitably remains at the bottom of the vial when drawing is performed), it is difficult for a user to input an appropriate sample volume, and thus, a trouble may occur, such as injection of bubbles.

As a problem unique to the programming method (a), there is the possibility of the vial volume being exceeded when several fractions are assembled.

As a problem unique to the programming method (b), there is a need for a mechanism for handling a sample volume of a plurality of fractions.

As a problem unique to the programming method (c), there is a need to prepare the instrument methods for the number of fractions. In the case where there is a great variation in the sample volume, it is difficult for a user to select an appropriate instrument method according to the sample volume.

As a problem unique to the programming method (d), there is a need for a task of rewriting the sample position and the volume for each sample by the pre-treatment program, and in the case where there is a great number of samples, adopting this method is not realistic.

The sample concentration methods described above are only examples, and description of the method of specifying the fraction volume and the number of fractions of a sample to be concentrated by the trap column, and of the method of controlling the solvent delivery pump according to the actual sample injection volume is omitted in the present invention; the present invention has its object to enable grasping of the actual sample injection volume without depending on the batch table or the programming method of the instrument method.

Solutions to the Problems

An autosampler of the present invention includes a flow path switching valve to which a sample push unit and an analysis flow path are connected, a sample loop connected to the flow path switching valve, a sampling needle connected to the flow path switching valve, a metering pump connected to the flow path switching valve, and a control unit for controlling operations of the flow path switching valve and the metering pump.

Furthermore, the control unit includes an injection/delivery control unit for switching the flow path switching valve so that the flow path switching valve configures a flow path for sample push for injecting a sample in a sample vial from the sampling needle into the sample loop by the metering pump, or a flow path for delivery for delivering a sample injected into the sample loop to an analysis flow path by a solvent from the sample push unit, and an injection volume addition unit for adding up injection volume of a same sample component injected into the sample loop.

In one mode, an example of the injection volume addition unit adds up the injection volume based on an instruction for the metering pump at a time of the injection/delivery control unit injecting a sample in the sample vial from the sampling needle into the sample loop by the metering pump.

In another mode, the control unit further includes an injectable volume calculation unit for calculating an injectable sample volume for each sample vial by retrieving from a preparative device a separation condition or a separation result at a time of separation of a sample into the sample vial and retrieving a remaining sample volume setting input to the control unit, and based on fraction information selected by a user. In this case, an example of the injection/delivery control unit is preferably configured to issue an instruction to the metering pump so that the metering pump draws in a sample in a sample vial within a range of injectable volume calculated by the injectable volume calculation unit for each sample vial.

According to this mode, the injectable sample volume may be automatically calculated from the separation result, and the burden on a user for batch table creation may be reduced.

In further another mode, this autosampler includes a sensor for detecting a sample volume in a sample vial. In this case, the control unit preferably further includes an injectable volume calculation unit for calculating an injectable sample volume for each sample vial by retrieving the sample volume detected by the sensor, and the injection/delivery control unit is preferably configured to issue an instruction to the metering pump so that the metering pump draws in a sample in a sample vial within a range of injectable volume calculated by the injectable volume calculation unit for each sample vial.

According to this mode, the injectable volume for each sample vial may be automatically calculated based on a signal retrieved from the sensor, and thus, the burden on a user for batch table creation may be reduced, and also, since injection of a sample by more than the injectable volume is not performed even with respect to a sample whose volume is not clear due to evaporation or the like, injection of the sample into the sample loop without suctioning of bubbles is made possible.

Effects of the Invention

The autosampler of the present invention includes the injection volume addition unit for adding up the injection volume of a same sample component that is injected into the sample loop, and thus, processes such as dilution may be performed according to the total sample volume that is input and the actual sample injection volume including additives and the like.

As an example of a process according to the actual sample injection volume, a sample concentration method by a trap column described with reference to a conventional technique may be cited. According to such a sample concentration method, the volume of a mobile phase delivered from the sample push unit and the volume of a diluent delivered from the make-up unit are dependent on the actual sample injection volume, and thus, if the actual sample injection volume is grasped by the present invention, the amount of consumption of the mobile phase and the diluent may be minimized.

Furthermore, according to the present invention, it is possible to check that the sample injection volume does not exceed the volume of the sample loop even when there are several injections from the batch table of the same component.

EMBODIMENTS OF THE INVENTION (Embodiment 1)

FIGS. 1 and 4 schematically show a sample concentration device provided with an autosampler 1 of an embodiment. The sample concentration device is a device for injecting a sample, and trapping (collecting) the sample in a trap column, and includes an autosampler 1 for injecting a certain amount of sample, a trap column 8, a sample push unit 5 for delivering a sample injected by the autosampler 1 to the trap column 8 by a solvent delivery pump 5a or 5b for sample push, a make-up unit 6 for compensating for a diluent by a solvent delivery pump 6a or 6b for make-up with respect to a sample pushed out by the sample push unit 5, and a controller 15 for controlling operations of the autosampler 1, the sample push unit 5, and the make-up unit 6.

The autosampler 1 includes an autosampler control unit 50 for controlling the operation of the autosampler 1.

The sample concentration device is sometimes incorporated in a liquid chromatograph as a part of the liquid chromatograph. In such a case, the trap column 8 is separated from a concentration device and is connected to an analysis system by a flow path switching valve, and a sample trapped in the trap column 8 is eluted by a solvent delivery pump for elution, and is analyzed in the column. The sample concentration device also includes such a mode, but in the embodiments, description of parts other than the concentration device is omitted.

At the autosampler 1, a sample loop 4 is connected between two ports of a high-pressure valve 2 as a flow path switching valve, and a sampling needle 30 is connected to another port of the high-pressure valve 2, and a syringe pump 3, which is a metering pump, is connected to further another port of the high-pressure valve 2. The sample push unit 5 is connected to further another port of the high-pressure valve 2, and the trap column 8 is connected to further another port of the high-pressure valve 2.

At the autosampler 1, a sample in a vial (sample container) 32 is drawn by the syringe pump 3 from the sampling needle 30 into the sample loop 4 (FIG. 4), and the high-pressure valve 2 is switched, and thus the sample drawn into the sample loop 4 is delivered to the trap column 8 by a solvent from the sample push unit 5 (FIG. 1).

At the autosampler 1, a drain valve 13 is connected between the syringe pump 3 and the high-pressure valve 2. After an injection process, a mobile phase that is drawn into a metering flow path of the syringe pump 3 from the sample loop 4 at the time of drawing of the sample is discharged from the drain valve 13.

At the autosampler 1, a cleaning port 34 for cleaning the sampling needle 30 is arranged, and a cleaning liquid 36 is connected to the syringe pump 3 via a switching valve 35. At the time of cleaning of the sampling needle 30 and the flow path from the high-pressure valve 2 to the sampling needle 30 in the injection state in FIG. 1, cleaning is performed by inserting the sampling needle 30 into the cleaning port 34 and drawing the cleaning liquid into the syringe pump 3 via the switching valve 35, and then, switching the switching valve 35, and discharging the cleaning liquid which was drawn into the syringe pump 3 from the sampling needle 30.

The flow path structure (the connection method of the high-pressure valve 2, the sample loop 4, and the sampling needle 30) of the autosampler 1 may take another structure. For example, a structure is possible where the syringe pump 3 on a separate flow path is directly connected to the sampling needle 30, an injection port is connected to another port of the high-pressure valve 2, and a sample is pushed into the sample loop 4. Also a structure is possible, for example, where the sample loop 4 is connected to one port of the high-pressure valve 2 and the sampling needle 30 is directly connected at its tip end, where the syringe pump 3 on a separate flow path is connected to the sampling needle 30, and where an injection port is connected to another port of the high-pressure valve 2, and after a sample is drawn into the sample loop 4 from the sampling needle 30 by the syringe pump 3, the sampling needle 30 is inserted into the injection port and the total volume of the sample in the sample loop 4 is injected into the flow path (total volume injection method).

Two solvent delivery pumps 5a and 5b for sample push are provided to the sample push unit 5, and these solvent delivery pumps 5a and 5b are connected to the high-pressure valve 2 in parallel, and thus, one of two types of solvents or a mixture thereof may be supplied. However, the sample push unit 5 may alternatively be provided with only one solvent delivery pump. Four types of solvents may be drawn into each of the solvent delivery pumps 5a and 5b, but the number of solvents is not limited thereto, and any number of types may be used including one type.

A three-way joint 7 is provided on the flow path through which a sample is transferred from the high-pressure valve 2 to the trap column 8, and the make-up unit 6 is connected via the three-way joint 7. The make-up unit 6 is for compensating for a diluent to dilute a sample.

Two solvent delivery pumps 6a and 6b are also provided to the make-up unit 6, and these solvent delivery pumps 6a and 6b are connected to the high-pressure valve 2 in parallel, and thus, one of two types of solvents or a mixture thereof may be supplied as a diluent. However, the make-up unit 6 may alternatively be provided with only one solvent delivery pump. Four types of solvents may be drawn into each of the solvent delivery pumps 6a and 6b, but the number of solvents is not limited thereto, and any number of types may be used including one type.

The controller 15 may be realized by a dedicated computer of the concentration device or of a liquid chromatograph in which the concentration device is installed, or may be realized by a general-purpose personal computer. Moreover, it may be realized by both the dedicated computer and the personal computer.

Figure 2:
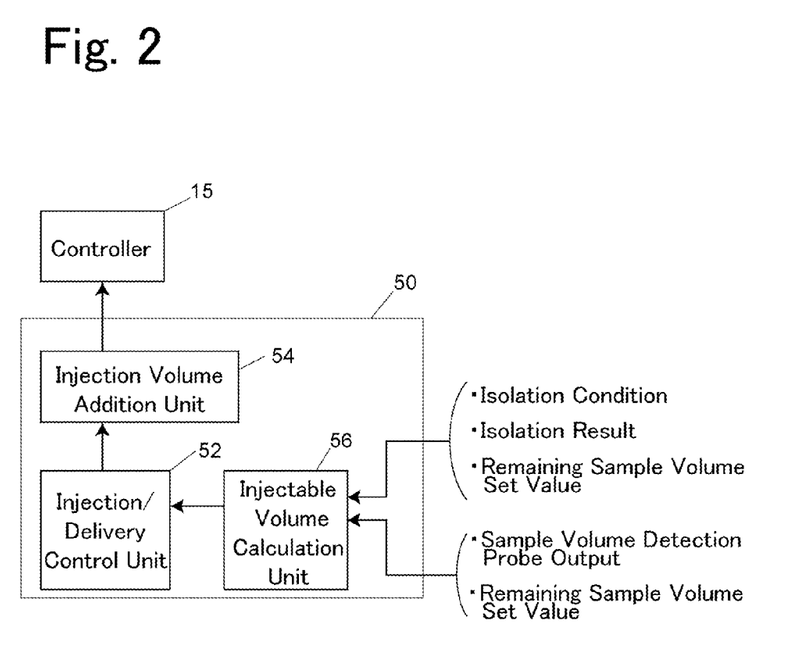
FIG. 2 is a block diagram for describing functions of an autosampler control unit of the autosampler of the present embodiment.

The autosampler control unit 50 of the autosampler 1 is a dedicated computer, and is provided with an injection/delivery control unit 52 and an injection volume addition unit 54, as shown in FIG. 2.

The injection/delivery control unit 52 switches the high-pressure valve 2 between a flow path structure for sample push for injecting a sample in the vial 32 from the sampling needle 30 into the sample loop 4 by the syringe pump 3 and a flow path structure for delivery for delivering a sample injected into the sample loop 4 to an analysis flow path by a solvent from the sample push unit 5.

The injection volume addition unit 54 adds up the injection volume of a same sample component injected into the sample loop 4.

An example of the injection volume addition unit 54 is for adding up the injection volume based on an instruction for the syringe pump 3 at the time of the injection/delivery control unit 52 injecting a sample in the vial 32 from the sampling needle 30 into the sample loop 4 by the syringe pump 3.

The autosampler control unit 50 of the autosampler 1 may further include an injectable volume calculation unit 56. The injectable volume calculation unit 56 calculates an injectable sample volume for each vial 32 by retrieving from a preparative device a separation condition or a separation result at the time of separation of a sample into the vial 32 and retrieving a remaining sample volume setting input to the autosampler control unit 50, and based on fraction information selected by a user. When the injectable volume calculation unit 56 is provided, the injection/delivery control unit 52 is configured to issue an instruction to the syringe pump 3 so that the syringe pump 3 draws in a sample in the vial 32 within the range of injectable volume calculated by the injectable volume calculation unit 56 for each vial 32.

The autosampler 1, the sample push unit 5, the make-up unit 6, and the controller 15 may be integrated, or they may be separate units.

The controller 15 performs a process of controlling the solvent delivery pumps 5a and 5b for sample push, the solvent delivery pumps 6a and 6b for make-up, and other units based on the injection volume notified by the autosampler control unit 50 of the autosampler 1.

In the embodiment, a trap concentration process dependent on the injection volume is performed. The injection volume that the autosampler control unit 50 of the autosampler 1 is to notify to the controller 15 is the injection volume added up by the injection volume addition unit 54, and it may be a sample volume input to the autosampler control unit 50, or in the case where addition/mixing of an additive or dilution is performed by the pre-treatment program, this may be taken into account with respect to the volume.

Additionally, the present system assumes delivery of a large volume, and thus, is an embodiment according to which the time program is started in the pre-treatment program to start delivery by the solvent delivery pump of the sample push unit 5, and then a sample is injected after the delivery becomes stable, but it is needless to say that sample injection may be swiftly performed by performing delivery by the solvent delivery pump also during idling, starting the time program, in the pre-treatment program, at the same time as injection is enabled, and starting delivery by the solvent delivery pumps of the sample push unit 5 and the make-up unit 6.

Figure 6:
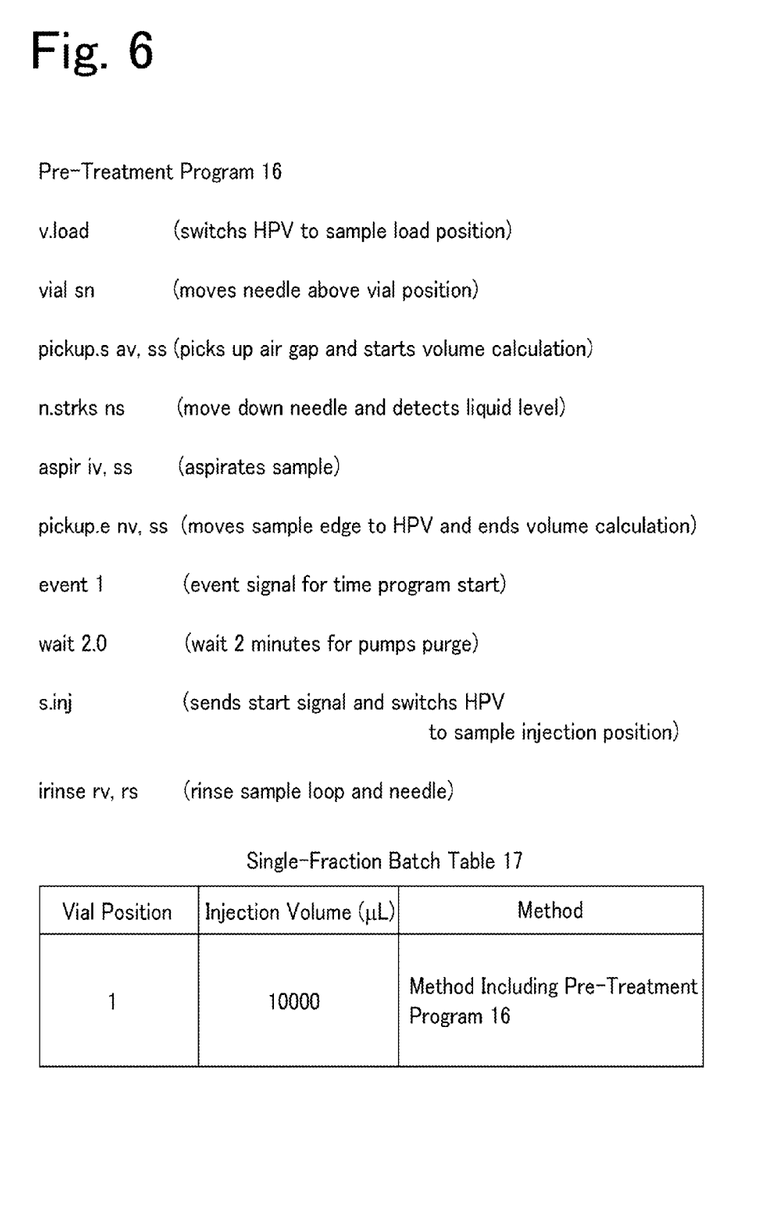
FIG. 6 is a diagram showing a batch table and a pre-treatment program for sample injection volume addition to be used by an autosampler of an embodiment where the number of fractions is one.

FIG. 6 shows a batch table and a pre-treatment program for calculating a sample injection volume of a sample fractionated into one vial and for performing sample injection.

The procedure for injecting a sample fractionated into one vial is programmed by a method including a pre-treatment program 16 and a single-fraction batch table 17 specifying the position of the sample fractionated into one vial.

In the pre-treatment program, drawing-in and discharging of a sample, an additive, and air are repeatedly performed due to drawing of the sample into the sample loop 4, movement inside the sample loop 4, drawing-in of an additive and mixing inside the vial 32, drawing-in of air and bubbling inside the vial, and the like, and thus, a program command for calculating at the drawing operation in which section of the pre-treatment program addition of the sample injection volume is to be performed is used.

Figure 5:
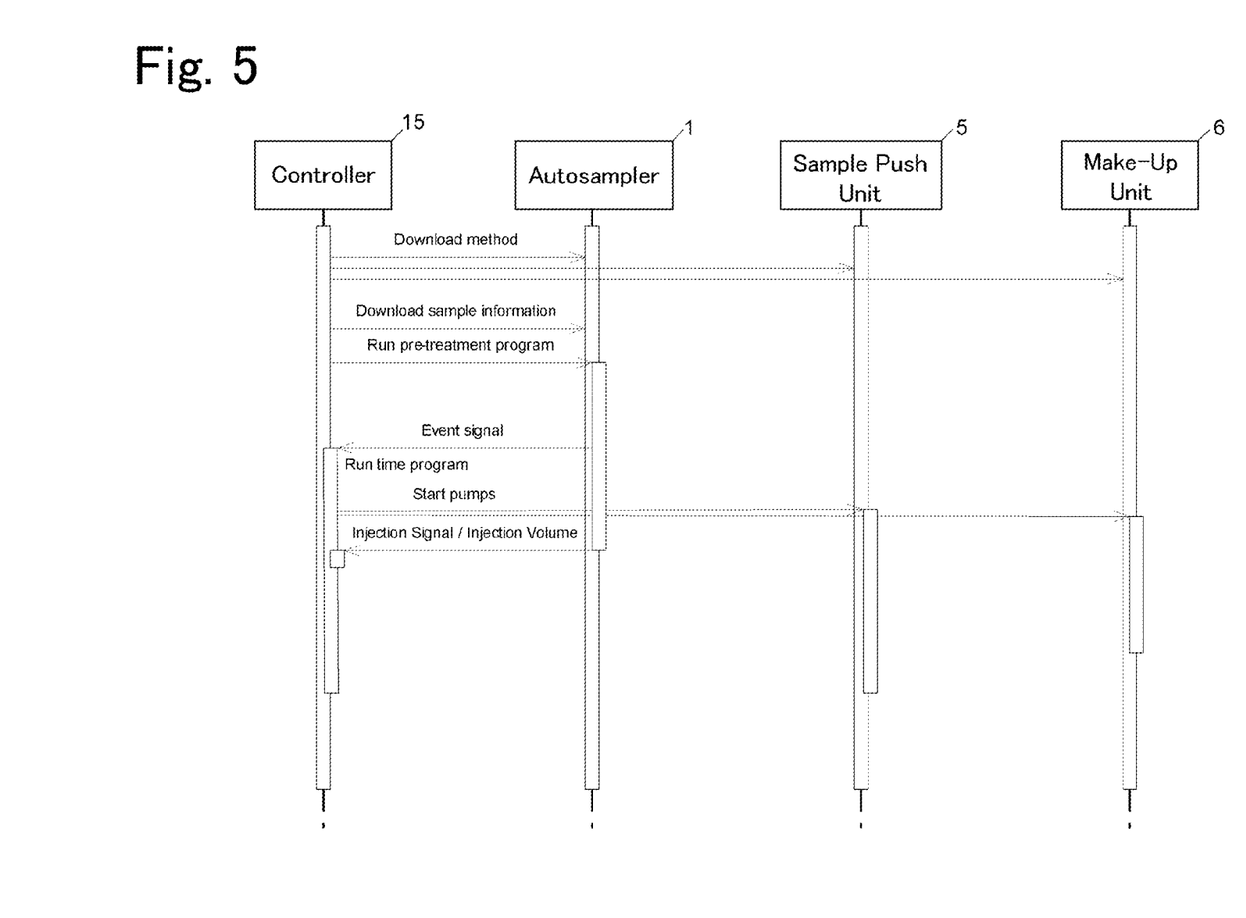
FIG. 5 is a time chart showing an operation of the sample concentration device.

A control method according to the present embodiment for performing sample concentration will be described with reference to the time chart in FIG. 5.

First, an instrument method for controlling the sample concentration device is downloaded from the controller 15 to the autosampler 1, the sample push unit 5, the make-up unit 6, and other necessary units (Download method).

The instrument method includes, in addition to parameters for controlling the autosampler 1, the sample push unit 5, and the make-up unit 6, a time program, a pre-treatment program, and the like.

The time program and the pre-treatment program may be executed by the controller 15, or by each of the autosampler 1, the sample push unit 5, and the make-up unit 6.

The pre-treatment program is a program including sequential run commands included in the instrument method, and includes as necessary, in addition to operations such as addition/mixing of an additive or dilution in the vial 32, discharging of a mobile phase in the metering flow path of the syringe pump 3 after injection, and cleaning of the sampling needle 30 and the flow path from the high-pressure valve 2 to the sampling needle 30, an operation of rewriting the sample position for drawing a sample at the autosampler 1 and the volume to be drawn that are normally specified in a batch table.

The time program is a program for determining the timings (analysis elapsed time of command execution) of controlling the operations of the autosampler 1, the sample push unit 5, the make-up unit 6, and other necessary units after output of a start signal (after an analysis is started), and includes the timings of controlling the operations of the sample push unit 5 and the make-up unit 6, but description of the control method of the solvent delivery pumps according to the actual sample injection volume is omitted from the present invention.

Next, the controller 15 downloads, to the autosampler 1, sample information such as the position of the vial of a sample, the injection volume, and the like (Download sample information).

Then, the controller 15 instructs the autosampler 1 to start the pre-treatment program (Run pre-treatment program).

According to the contents of the pre-treatment program, the autosampler 1 switches the high-pressure valve 2 to the sample metering position (the state in FIG. 4), and starts a sample drawing operation.

After the sample drawing operation, the autosampler 1 transmits to the controller 15, according to the contents of the pre-treatment program, an event signal for starting the time program (Event signal), and the controller 15 starts the time program (Run time program). The event signal may be a digital signal generated by software, or may be an analog signal such as a relay signal.

The controller 15 receives the event signal, and causes the sample push unit 5, the make-up unit 6, and other necessary units to perform an analysis operation including execution of the time program (Start pumps). This is taken as the start time of the time program.

According to the contents of the pre-treatment program, at the time of switching the high-pressure valve 2 to the injection position (the state in FIG. 1), the autosampler 1 notifies the controller 15 of an injection start signal and the sample injection volume (Injection Signal/Injection Volume).

In the following, an operation of adding up the actual sample injection volume by the pre-treatment program will be described.

To trap a sample, the controller 15 executes one row in the batch table 17. The control unit 50 of the autosampler 1 executes the pre-treatment program 16, and sequentially performs the following processes to introduce the sample into the sample loop 4.

The high-pressure valve 2 is switched to a load position (FIG. 4) (v.load command).

The sampling needle 30 is moved to directly above the vial 32 specified in the batch table 17 (vial command).

After an air gap for preventing mixing of the cleaning liquid inside the sample loop 4 and the sample is drawn in, the adding up of the sample injection volume is started (pickup.s command).

The sampling needle 30 is lowered (n.strk command).

The sample volume specified in the batch table 17 is drawn in (aspir command).

The sample end at the tip end of the sampling needle 30 is moved to the high-pressure valve 2, and the adding up of the sample injection volume is ended (pickup.e command).

An event signal is transmitted from the control unit 50 to the controller 15 to start delivery by the solvent delivery pump 5a or 5b for sample push and the solvent delivery pump 6a or 6b for make-up, and to perform flow path purge (event command).

The end of the flow path purge is waited for two minutes (wait command).

The control unit 50 notifies the controller 15 to inject a sample and perform an analysis, switches the high-pressure valve 2 to the injection position (FIG. 1), and notifies the controller 15 of the added-up sample injection volume (s.inj).

The sample loop 4 and the sampling needle 30 are cleaned (irinse).

The controller 15 is capable of controlling the solvent delivery pump 5 for sample push, the solvent delivery pump 6 for make-up, and other units according to the sample injection volume added up by the pre-treatment program, but description of the control method thereof is omitted in the present invention.

Figure 7A:
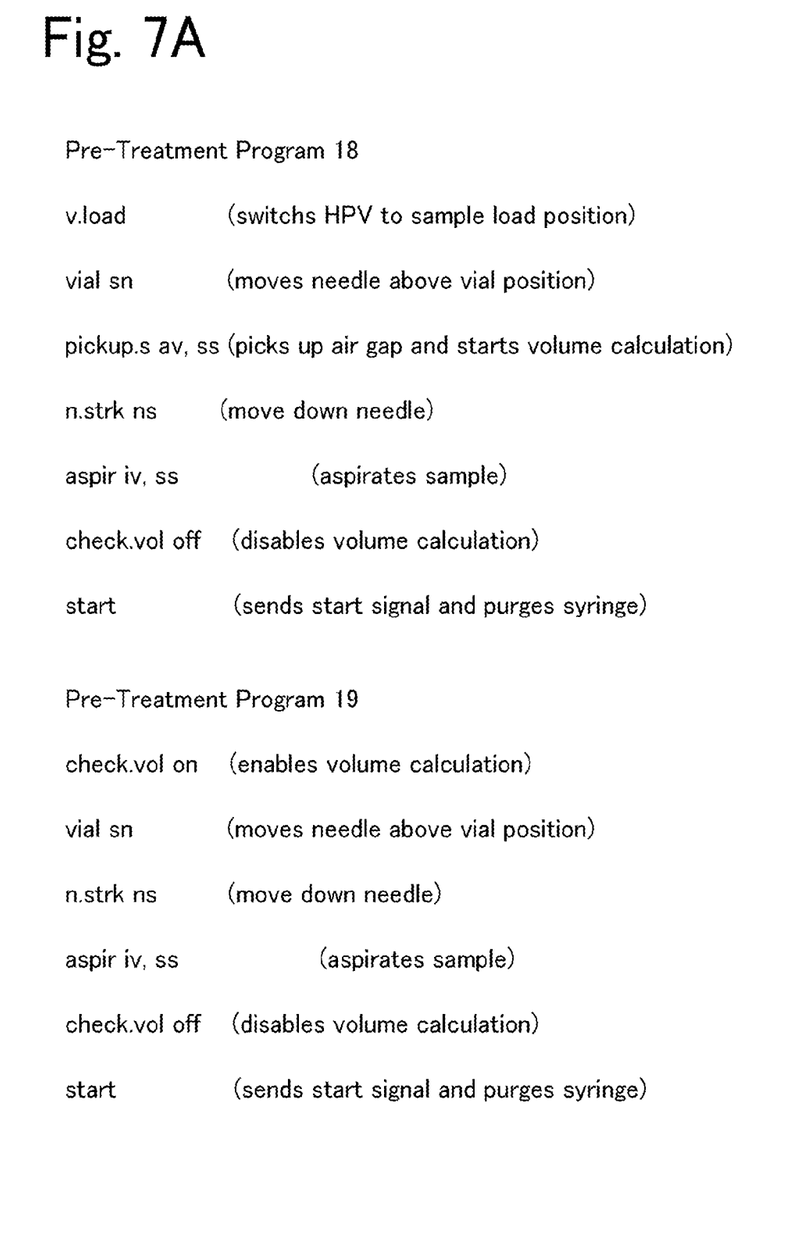
FIGS. 7A and 7B illustrate a diagram showing a batch table and a pre-treatment program for sample injection volume addition to be used by an autosampler of an embodiment where there are several fractions.
Figure 7B:
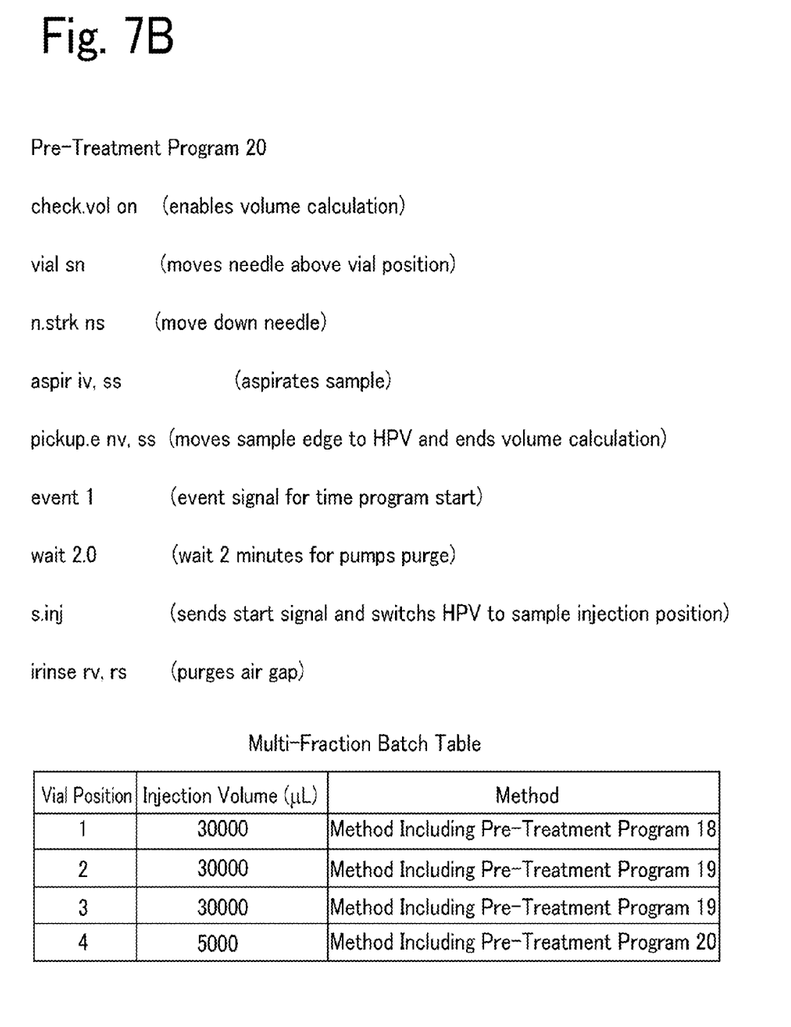

Next, a batch table and a pre-treatment program for calculating the sample injection volume of a sample fractionated into a plurality of vials and for performing sample injection will be described with reference to FIGS. 7A and 7B. The procedure for injecting a sample fractionated into a plurality of vials is programmed by three methods including pre-treatment programs 18 to 20, and a multi-fraction batch table 21 specifying the positions of the sample fractionated into a plurality of vials.

To trap a first sample, the controller 15 executes the first row in the batch table 21.

The control unit 50 of the autosampler 1 executes the pre-treatment program 18, and performs the following processes to introduce the first sample into the sample loop 4.

The high-pressure valve 2 is switched to a load position (v.load command).

The sampling needle 30 is moved to directly above the vial specified in the batch table 21 (vial command).

After an air gap for preventing mixing of the cleaning liquid inside the sample loop 4 and the sample is drawn in, the adding up of the sample injection volume is started (pickup.s command).

The sampling needle 30 is lowered (n.strk command).

The sample volume specified in the batch table 21 is drawn in (aspir command).

The adding up of the sample injection volume is interrupted (check.vol command).

The control unit 50 of the autosampler 1 notifies the controller 15 to perform an analysis without injecting a sample, and then switches the drain valve 13 to the drain position, purges the syringe 3, and finally switches the drain valve 13 to the high-pressure valve 2 side (start command).

To trap intermediate samples, the controller 15 executes the second and the third rows in the batch table 21. The control unit 50 of the autosampler 1 executes the pre-treatment program 19, and performs the following processes to introduce the intermediate sample into the sample loop 4.

The adding up of the sample volume is restarted (check.vol command).

The sampling needle 30 is moved to directly above the vial specified in the batch table 21 (vial command).

The sampling needle 30 is lowered (n.strk command).

The sample volume specified in the batch table 21 is drawn in (aspir command).

The adding up of the sample injection volume is interrupted (check.vol command).

The control unit 50 of the autosampler 1 notifies the controller 15 to perform an analysis without injecting a sample, and then switches the drain valve 13 to the drain position, purges the syringe 3, and finally switches the drain valve 13 to the high-pressure valve 2 side (start command).

To inject the last sample, the controller 15 executes the fourth row in the batch table 21. The control unit 50 of the autosampler 1 executes the pre-treatment program 20 and performs the following processes to introduce the last sample into the sample loop 4.

The adding up of the sample volume is restarted (check. vol command).

The sampling needle 30 is moved to directly above the vial specified in the batch table 21 (vial command).

The sampling needle 30 is lowered (n.strk command).

The sample volume specified in the batch table 21 is drawn in (aspir command).

The sample end at the tip end of the sampling needle 30 is moved to the high-pressure valve 2, and the adding up of the sample injection volume is ended (pickup.e command).

An event signal is transmitted to the controller 15 to start delivery by the solvent delivery pump of the sample push unit 5 and the solvent delivery pump of the make-up unit 6, and to perform flow path purge (event command).

The end of the flow path purge is waited for two minutes (wait command).

The control unit 50 of the autosampler 1 notifies the controller 15 to inject a sample and perform an analysis, switches the high-pressure valve 2 to the injection position (FIG. 1), and notifies the controller 15 of the added-up sample injection volume (s.inj).

The sample loop 4 and the sampling needle 30 are cleaned (irinse).

At this time, in the case where the volume obtained by adding up the sample volume reaches the volume of the sample loop 4, the sample is no longer drawn in by the aspir command.

As an example modification, when the volume obtained by adding up the sample volume reaches the volume of the sample loop 4, it is also possible to incorporate condition determination for cancelling the operation of moving the sampling needle 15 or the operation itself of drawing in the sample.

Also, as an example modification, it is possible to interrupt the adding up of the sample volume by the start command or the s.inj command, but since there are cases where the sample volume should not be added up, such as when reciprocating the syringe 3 in the case of performing addition of an additive or dilution, a function for interrupting and restarting the adding up of the sample volume (check. vol command) is desirably provided.

The solvent delivery pump 5 for sample push, the solvent delivery pump 6 for make-up, and other units may be controlled by the pre-treatment program according to the added-up sample injection volume, but description of the control method thereof is omitted in the present invention.

In this embodiment, trap concentration of a sample fractionated by a preparative LC/LCMS may be performed by the method of adding up the volume of the sample fractionated into a plurality of vials and the autosampler control method in FIG. 4.

In the case of not taking evaporation into account, the volume of the sample fractionated into a plurality of vials is obtained as the product of the fraction band width (unit: minute) and the flow rate.

Based on the separation condition (flow rate), the separation result (vial position, and fraction band width), and the remaining sample volume setting, the injectable sample volume of a specified fraction may be automatically calculated, and the batch table to be used by an autosampler for liquid chromatograph analysis may be automatically created.

Figure 8:
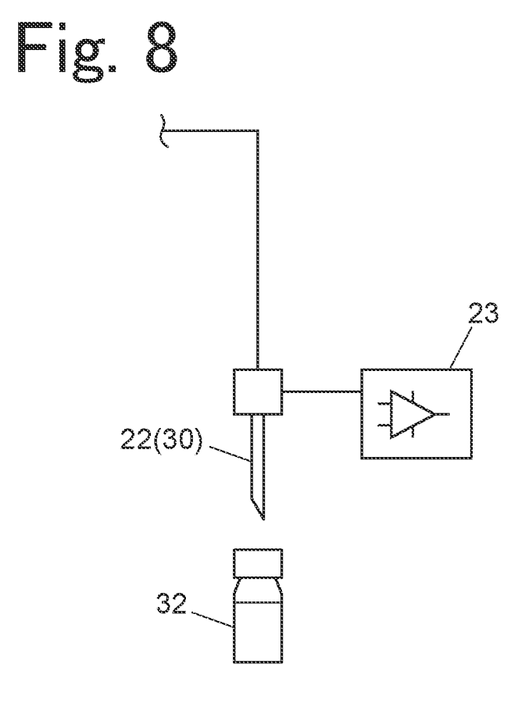
FIG. 8 is a schematic diagram showing a sample volume detection probe according to another embodiment.

As further another embodiment, a method of detecting the sample volume by a detection probe 22 at the autosampler 1 is shown in FIG. 8. The detection probe 22 is the sampling needle 30 used as a sensor for detecting the sample volume, and detects the sample liquid surface based on a change in the capacitance or permittivity.

The autosampler 1 includes a liquid surface detection unit that takes an output of the liquid surface detection probe 22 that is integrated with the sampling needle 30 as an input, that performs amplification/conversion by a liquid surface detection circuit 23 configured from an amplifier, a comparator, an AD converter or the like, and that outputs a change in the physical properties of the air and the sample solvent (mainly, a change in the capacitance or permittivity).

In this embodiment, the injectable sample volume is determined based on the height of the liquid surface detected by the detection probe 22 (the detected sample volume), the setting regarding the height of the needle at the time when the limit of the sample drawing is reached (the remaining sample volume setting), and the setting regarding the shape of the sample vial/test tube.

In this embodiment, the injectable volume calculation unit 56 of the control unit 50 of the autosampler 1 retrieves the sample volume detected by the liquid surface detection probe 22, and calculates the injectable sample volume of each vial 32. Then, the injection/delivery control unit 52 issues an instruction to the syringe pump 3 so that the syringe pump 3 draws in a sample in the vial 32 within the range of injectable volume calculated for each vial 32 by the injectable volume calculation unit 56.

With the function for drawing in a sample volume (aspir command) of the pre-treatment programs 16 and 18 to 20, drawing in of the injectable volume calculated based on a detection signal of the detection probe 22 is performed with the sample volume specified in the batch table 17 or 21 as the upper limit. Thus, the maximum vial volume or the maximum fraction volume is specified as the sample volume in the batch table to be used by the autosampler for liquid chromatograph analysis.

DESCRIPTION OF REFERENCE SIGNS

1: Autosampler
2: High-pressure valve
3: Syringe pump
4: Sample loop
5: Sample push unit
6: Make-up unit
7: Three-way joint
8: Trap column
9: Fraction component for vial #1 (only component A)
10: Fraction component for vial #2 (only component A)
11: Fraction component for vial #3 (components A and B)
12: Fraction component for vial #4 (only component A)
13: Drain valve
15: Controller
22: Detection probe
23: Liquid surface detection circuit
30: Sampling needle
32: Vial
34: Cleaning port
35: Switching valve 36: Cleaning liquid
50: Control unit of autosampler
sn: Sample number
av: Air gap volume
ss: Sampling speed
ns: Needle stroke
iv: Sample volume (injection volume)
nv: Needle loop volume
rv: Rinsing volume
rs: Rinsing speed

What is claimed is:

1. An autosampler comprising: a flow path switching valve to which a sample push unit and an analysis flow path are connected; a sample loop connected to the flow path switching valve; a sampling needle connected to the flow path switching valve; a metering pump connected to the flow path switching valve; and a control unit for controlling operations of the flow path switching valve and the metering pump, wherein the control unit includes an injection/delivery control unit for switching the flow path switching valve on that the flow path switching valve configures a flow path for sample push for injecting a sample in a sample vial from the sampling needle into the sample loop by the metering pump, or a flow path for delivery for delivering a sample injected into the sample loop to an analysis flow path by a solvent from the sample push unit, and an injection volume addition unit for adding up injection volumes of a same sample component injected into the sample loop a plurality of times.

2. The autosampler according to any of claim 1, wherein the injection volume addition unit is for adding up the injection volume based on an instruction for the metering pump at a time of the injection/delivery control unit injecting a sample in the sample vial from the sampling needle into the sample loop by the metering pump.

3. An autosampler comprising:
a flow path switching valve to which a sample push unit and an analysis flow path are connected;
a sample loop connected to the flow path switching valve;
a sampling needle connected to the flow path switching valve;
a metering pump connected to the flow path switching valve; and
a control unit for controlling operations of the flow path switching valve and the metering pump,
wherein the control unit includes
an injection/delivery control unit for switching the flow path switching valve so that the flow path switching valve configures a flow path for sample push for injecting a sample in a sample vial from the sampling needle into the sample loop by the metering pump, or a flow path for delivery for delivering a sample injected into the sample loop to an analysis flow path by a solvent from the sample push unit, and
an injection volume addition unit for adding up injection volume of a same sample component injected into the sample loop,
wherein the control unit further includes an injectable volume calculation unit for calculating an injectable sample volume for each sample vial by retrieving from a preparative device a separation condition or a separation result at a time of separation of a sample into the sample vial and retrieving a remaining sample volume setting input to the control unit, and based on fraction information selected by a user, and
wherein the injection/delivery control unit is configured to issue an instruction to the metering pump so that the metering pump draws in a sample in a sample vial within a range of injectable volume calculated by the injectable volume calculation unit for each sample vial.

4. An autosampler comprising:
a flow path switching valve to which a sample push unit and an analysis flow path are connected;
a sample loop connected to the flow path switching valve;
a sampling needle connected to the flow path switching valve;
a metering pump connected to the flow path switching valve; and
a control unit for controlling operations of the flow path switching valve and the metering pump,
wherein the control unit includes
an injection/delivery control unit for switching the flow path switching valve so that the flow path switching valve configures a flow path for sample push for injecting a sample in a sample vial from the sampling needle into the sample loop by the metering pump, or a flow path for delivery for delivering a sample injected into the sample loop to an analysis flow path by a solvent from the sample push unit, and
an injection volume addition unit for adding up injection volume of a same sample component injected into the sample loop,
wherein the autosampler includes a sensor for detecting a sample volume in a sample vial,
wherein the control unit further includes an injectable volume calculation unit for calculating an injectable sample volume for each sample vial by retrieving the sample volume detected by the sensor, and
wherein the injection/delivery control unit is configured to issue an instruction to the metering pump so that the metering pump draws in a sample in a sample vial within a range of injectable volume calculated by the injectable volume calculation unit for each sample vial.

5. The autosampler according to any of claim 3, wherein the injection volume addition unit is structured for adding up the injection volume based on an instruction for the metering pump at a time of the injection/delivery control unit injecting a sample in the sample vial from the sampling needle into the sample loop by the metering pump.

6. The autosampler according to any of claim 4, wherein the injection volume addition unit is structured for adding up the injection volume based on an instruction for the metering pump at a time of the injection/delivery control unit injecting a sample in the sample vial from the sampling needle into the sample loop by the metering pump.

* * * * *